United States Patent [19]
Swadesh et al.

[11] Patent Number: 5,898,033
[45] Date of Patent: Apr. 27, 1999

[54] ANTIGEN-PROCESSING CELL-TARGETED CONJUGATES

[76] Inventors: Joel K. Swadesh, 285 Plantation St., No. 718, Worcester, Mass. 01604; Martin Sevoian, 167 Montague Rd., North Amherst, Mass. 01059

[21] Appl. No.: 08/994,334

[22] Filed: Dec. 19, 1997

Related U.S. Application Data

[63] Continuation of application No. 08/475,528, Jun. 7, 1995, abandoned.

[51] Int. Cl.$^6$ .......................... A61K 31/19; A61K 31/54
[52] U.S. Cl. ..................... 514/224.2; 514/570; 514/616; 514/814; 514/825; 528/328
[58] Field of Search ................................... 514/616, 570, 514/224.2, 825, 824; 528/328

[56] References Cited

U.S. PATENT DOCUMENTS

| | | |
|---|---|---|
| 4,151,173 | 4/1979 | Vogel . |
| 4,349,530 | 9/1982 | Royer . |
| 4,356,166 | 10/1982 | Peterson et al. . |
| 4,386,026 | 5/1983 | Ponpipom et al. . |
| 5,030,834 | 7/1991 | Krumdieck et al. . |
| 5,118,784 | 6/1992 | Kubota et al. . |
| 5,225,182 | 7/1993 | Sharma . |

FOREIGN PATENT DOCUMENTS

| | | | |
|---|---|---|---|
| 0 094 844 | 11/1983 | European Pat. Off. | ........ A61K 47/00 |
| 0 485 157 | 11/1991 | European Pat. Off. | ........ C08B 37/08 |
| 0 485 158 | 11/1991 | European Pat. Off. | ........ C08B 37/00 |
| WO 87/03891 | 7/1987 | WIPO | ............. C08G 69/10 |
| WO 92/05802 | 4/1992 | WIPO | ............. A16K 39/44 |
| WO 92/19248 | 11/1992 | WIPO . | |

OTHER PUBLICATIONS

De Marre, et al., "Evaluation of the hydrolytic and enzymatic stability of macromolecular Mitomyci C derivatives", *Journal of Controlled Release*, 31:89–97, (1994).

Franssen, et al., "Hepatic and Intrahepatic Targeting . . . And Neoglycoproteins As Carrier Molecules", *Biochemical Pharmacology*, 45:1215–1226, (1993).

Liso, et al., "Antinociceptive and antipyretic properties . . . controlled delivery system", *Journal of Controlled Release*, 33:429–436, (1994).

Roos, et al., "Physicochemical and antitumor . . . of mitomycin C", *International Journal of Pharmaceutics*, 22:75–87, (1984).

van Heeswijk, et al., "The Synthesis and Characterization of Polypeptide . . . with Adriamycin. Part 1", *Journal of Controlled Release*, 1:301–315, (1985).

Anderson, "In Vitro and In Vivo Studies of Drug–Releasing Poly(amino acids)," *Annals New York Academy of Sciences*, 67–75 (1985).

Borbély et al., "Biosynthesis and Chemical Modification of Poly(–glutamic acid)," *Polymer Bulletin* 32, 127–132 (1994).

Goodman et al., "Immunochemical Studies on the Poly—D–glutamyl Capsule of Bacillus Anthracis. I. Characterization of the Polypeptide and of the Specificity of Its Reaction With Rabbit Antisera," *Biochemistry* 5, No. 2 657–664 (1966).

Goodman et al., "Immunochemical Studies on the Poly—D–glutamyl Capsule of Bacillus Anthracis. III. The Activity with Rabbit Antisera of Peptides Derived from the Homologous Polypeptide," *Biochemistry* 7, No. 2 706–710 (1968).

Jensen et al., "Production of Recombinant Human Growth Hormone in *Escherichia coli*: Expression of Different Precursors and Physiological Effects of Glucose, Acetate, and Salts," *Biotechnology and Bioengineering*, 36 1–11 (1990).

Nitecki et al., "Immunochemical Studies on the Poly (–glutamyl Capsule of Bacillus anthracis. II. The Synthesis of Eight Dipeptides and Four Tripeptides of Glutamic Acid," *Biochemistry* 5, 665–672 (1966).

Shah et al., "New Polymers Derived From Natural Origin–Poly(Glutamic Acid)," *Polymer Preprints*, 33 No. 2 488–490 (1992).

Thorne et al., "Production of Glutamyl Polypeptide By Bacillus Subtilis," *Journal of Bacteriology*, 68 307–315 (1954).

Tsukada et al., "An Anti–α–Fetoprotein Antibody–Daunorubicin Conjugate With A Novel Poly–L–glutamic Acid Derivative as Intermediate Drug Carrier," *JNCI*, 73, No. 3 721–729 (1984).

*Primary Examiner*—Keith D. MacMillan
*Attorney, Agent, or Firm*—Fish & Richardson P.C.

[57] ABSTRACT

An anti-inflammatory conjugate including a polyamino acid backbone, a non-steroidal anti-inflammatory agent, and a moiety linking the anti-inflammatory agent to the backbone, wherein the polyamino acid backbone has a molecular weight greater than 250 kD.

18 Claims, No Drawings

ANTIGEN-PROCESSING CELL-TARGETED CONJUGATES

This is a continuation of U.S. application Ser. No. 08/475,528, filed Jun. 7, 1995, abandoned.

BACKGROUND OF THE INVENTION

The invention relates to compositions of matter targeted to antigen-processing cells.

An antigen-processing cell is a leukocyte capable of secreting proteases or reactive-oxygen intermediates, or a leukocyte capable of internalizing and processing a protein, a carbohydrate, a polynucleic acid, or bacterium, and subsequently presenting a processed form thereof on its cell surface. Circulating leukocytes can internalize foreign particles by three mechanisms, the first being active phagocytosis, the second being passive, concentration gradient-dependent adsorption, and the third being active transport. Antigen-processing cells therefore include granulocytes (e.g., eosinophils, or polymorphonuclear neutrophils), macrophages, and monocytes.

In addition to antigen processing, antigen-processing cells perform proliferative and secretory functions. Certain antigen-processing cells circulate throughout the body, via the vascular system. Circulating antigen processing cells may or may not circulate through the lymph system. Examples of circulating antigen-processing cells include eosinophils, polymorphonuclear neutrophils, macrophages, lymphocytes, and monocytes. Examples of non-circulating antigen-processing cells include Kupffer cells in the liver, and microglial cells.

SUMMARY OF THE INVENTION

The invention is based, in part, on the discovery that circulating antigen-processing cells have an affinity for polyamino acids, such as poly-glutamic acid. When linked to or loaded with a therapeutic agent, the polyamino acids form conjugates that are useful to deliver the therapeutic agent to antigen-processing cells. Polyamino acids have a multiplicity of sites for linking therapeutic agents. A single conjugate can thus carry numerous therapeutic agent moieties. For example, a high molecular weight, insoluble, anti-inflammatory conjugate can be injected or implanted. Hydrolysis releases the therapeutic agent locally.

In one aspect, the invention features an anti-inflammatory conjugate including a polyamino acid backbone, a nonsteroidal anti-inflammatory agent, and a moiety linking the anti-inflammatory agent to the backbone, wherein the backbone has a molecular weight greater than 250 kD. The polyamino acid backbone is substantially made of poly-$\gamma$-glutamic acid.

In a second aspect, the invention features an anti-inflammatory conjugate targeted to a circulating antigen-processing cell. The superscript m indicates the residue number. The conjugate includes a derivatized polyamino acid of the formula: H—{—NH—C*H(—$X^m M^m Y^m$)—$(CH_2)_n$—(C=O)—$\}_p$—OH. Each $X^m$ independently is $C_{1-12}$ alkylene or deleted. Each $M^m$ independently is (C=O)—O, (C=O)—NH, or (C=O)—S, wherein the carbon atom of $M^m$ is bonded to $X^m$ or, when $X^m$ is deleted, to C*. Each $Y^m$ independently is H, $C_{1-12}$ alkyl, —$(CH_2)_a$—O—$(CH_2)_b$H, or a nonsteroidal anti-inflammatory agent, wherein at least one $Y^m$ is a nonsteroidal anti-inflammatory agent. Each of a and b, independently, is an integer between 0 and 12; p is the average total number of residues and is an integer between 1,900 and 15,000; m is an integer ranging between 1 and p. Each n is independently an integer between 0 and 5. The backbone has a molecular weight greater than 250 kD.

In another aspect, the invention features a method of treating an inflammatory disease in a mammal by administering to the mammal an effective amount of a conjugate of the invention as described above. A preferred mode of administration is subcutaneous implantation.

In another aspect, the invention features a method of targeting an anti-inflammatory agent to a circulating antigen-processing cell in a mammal, by obtaining an anti-inflammatory conjugate of the invention and injecting an amount of the anti-inflammatory conjugate into the mammal, thereby delivering an effective amount of the anti-inflammatory agent to a circulating antigen-processing cell in the mammal.

Targeting a therapeutic agent decreases the administered dosage required for effective treatment, and therefore decreases side effects of the therapeutic agent. In addition, targeting a therapeutic agent increases the ratio of effective dose to administered dose, thus enabling therapeutic use of agents previously believed to be too toxic when administered without a targeting mechanism. Disclosed conjugates are useful in treating autoimmune and inflammatory diseases mediated by antigen-processing cells such as systemic lupus erythematosus (SLE), rheumatoid arthritis, and type I diabetes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION OF THE INVENTION

The invention generally relates to conjugates which are targeted to vascularly circulating antigen-processing cells such as eosinophils, polymorphonuclear neutrophils, monocytes, lymphocytes, and macrophages. A conjugate of the invention includes a polyamino acid targeting agent, an anti-inflammatory therapeutic agent, and a linking moiety connecting the targeting agent to the therapeutic agent. More specifically, a conjugate of the invention includes a polyamino acid backbone having a multiplicity of side chains. At least one of the side chains terminates with a therapeutic agent.

TARGETING AGENT

The targeting agent is a polyamino acid backbone having an average molecular weight greater than 250 kD. As used herein, a "polyamino acid backbone" includes between 1,900 and 15,000 amino acids, and preferably includes between 4,000 and 12,000 amino acids. The considerable molecular weight of the backbone generally produces an insoluble conjugate that is slowly hydrolyzed, thus slowly releasing the therapeutic agent linked to the backbone. The molecular weight of the backbone helps to target the conjugate to the targeted cells.

Amino acids in the polyamino acid may be the same or different and are selected from naturally-occurring and non-naturally-occurring amino acids having a functionalizable side chain. A functionalizable side chain has at least one of the following functional groups: amino, hydroxyl, thiol, carboxylic acid, and thiocarboxylic acid group. A functional group can be attached to either a middle or terminal carbon atom of the side chain. Examples of an amino acid with a functionalizable side chain include glutamic acid and aspartic acid. Preferably, a polyamino acid is made of multiple units of a single, naturally-occurring amino acid. In addition, it is preferable that the polyamino acid backbone be nontoxic, non-immunogenic and biodegradable. Poly-γ-glutamic acid is one example of a preferred polyamino acid. A polyamino acid backbone has a geometry selected from generally linear, crosslinked, circular, helical, starburst or dendritic, chain (linked loops), or a combination thereof. A backbone which is substantially made of poly-γ-glutamic acid contains at least 80% poly-γ-glutamic acid residues.

THERAPEUTIC AGENTS

An anti-inflammatory therapeutic agent is a non-steroidal anti-inflammatory drug (NSAID) (or agonist thereof) that has been chemically modified in the process of linking the NSAID to a conjugate. However, the chemical modification must not so adversely affect the anti-inflammatory activity as to render the conjugate therapeutically ineffective. NSAIDs include 15-deoxyspergualin, piroxicam, ibuprofen, and acetylsalicylic acid. According to the invention, each conjugate must bear at least one anti-inflammatory agent. The load or concentration of anti-inflammatory agent per conjugate varies between 1 anti-inflammatory agent per conjugate and 100% loading of the functionalizable groups per conjugate (e.g., between 30 and 80% loading of the functionalizable groups on a conjugate).

In another aspect, the invention features a conjugate wherein the therapeutic agent is replaced by another moiety, such as a detectable label, which is targeted in a similar manner to antigen-processing cells.

LINKING MOIETIES

An anti-inflammatory agent is linked to the polyamino acid backbone by a linking moiety which covalently bonds the therapeutic agent to the polyamino acid backbone. Examples include a single covalent bond, an amide bond, an ester bond, and a thioester bond. Preferably, the linking moiety is hydrolyzed in vivo at a therapeutically useful rate. In general, a linking moiety is formed by a condensation reaction between a functional group on a side chain of the polyamino acid and a second functional group (e.g., amino, hydroxyl, carboxyl, or thiol) on the NSAID or modified NSAID. A linking moiety can be any chemical moiety that does not substantially interfere with either the therapeutic efficacy of the anti-inflammatory agent or the targeting efficacy of the polyamino acid backbone.

CONJUGATES

In one aspect, a conjugate of the invention has the following formula:

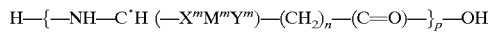

Superscript m corresponds to the residue number (i.e., in the first residue, $C^*$ is bonded to a moiety—$X^1M^1Y^1$, which may or may not be the same as the moiety —$X^2M^2Y^2$ which is bonded to $C^*$ of the second residue). Each $X^m$ is independently $C_{1-12}$ alkylene, $C_{2-12}$ poly- (alkyleneoxy), or deleted. Each $M^m$ is independently a linking moiety selected from bivalent ester (C=O)—O, amide (C=O)—NH, and thioester (C=O)—S moieties. The carbon atom of $M^m$ is bonded to $X^m$ or, when $X^m$ is deleted, to $C^*$. In one embodiment, each $M^m$ is independently selected from ester and amide moieties; in another embodiment, $X^m$ is deleted. Each $Y^m$ is independently H, $C_{1-12}$ alkyl, —$(CH_2)_a$—O—$(CH_2)_b$H, or a nonsteroidal anti-inflammatory agent, wherein at least one $Y^m$ is a nonsteroidal anti-inflammatory agent. Each of a and b independently is an integer between 0 and 12. In some embodiments, each of a and b independently are between 0 and 8, or between 0 and 4. In addition, p is an integer between 1,900 and 15,000 (e.g., between 4,000 and 10,000 or between 9,000 and 14,000) representing an average number of amino acids per polyamino acid backbone; m represents the residue number and is an integer value ranging between 1 and p; and each n is independently an integer between 0 and 5 (e.g., n is 0, n is 2, or n is between 3 and 5). Finally, the stereochemistry of each chiral carbon $C^*$ is independently L or D, although it is preferred that the stereochemistry of all $C^*$ in a given conjugate is the same, either all L or all D.

A conjugate of the invention has a molecular weight greater than 250 kD (e.g., between 250 kD and 500 kD, between 500 kD and 1500 kD, or between 1000 kD and 1500 kD) since the polyamino acid backbone has a molecular weight greater than 250 kD. Molecular weights can be measured by methods known to those in the art, such as gel permeation chromatography-multiple angle laser light scattering. In some embodiments, detectable imaging agents such as radiolabelled or fluorescent agents are linked to the conjugate. However, moieties that would result in the conjugate becoming a glycopeptide (e.g., carbohydrate moieties) are expressly excluded from the present invention.

SUSTAINED RELEASE

Conjugates of the invention are designed for various sustained release formulations, which are particularly suitable for chronic diseases. In general, a therapeutic agent delivered by a conjugate of the invention must be cleaved by a protease or other enzymes to be released by, e.g., a granulocyte or a phagocytic cell. In some embodiments, the conjugate must also be internalized (e.g., phagocytosized) before the therapeutic agent, cleaved or uncleaved, can exert its effect.

The rate of hydrolysis or release is controlled in part by altering the length of the polymer backbone (size). The size of a particle determines the ratio of effective surface area to volume; the lower the surface area to volume ratio, the slower the release rate. Crosslinking a partially-loaded conjugate with hexane diamine therefore reduces the release rate. Furthermore, the metabolism or hydrolysis (e.g., acid or base catalyzed) of a densely-loaded backbone is generally slower than a sparsely-loaded one.

The polar or nonpolar character of the conjugate also affects the rate of hydrolysis. Increased hydrophobicity typically reduces the release rate, by impeding access of degradative enzymes. Hydrophobicity is altered by reacting some functionalizable groups on a conjugate with hydrophobic (e.g., aliphatic or aromatic) ligands. Altering the overall charge of the conjugate, for example by adding an aspartic acid residue or an arginine residue, also affects the hydrolysis rate.

Finally, the chemical nature of the linking moiety between the backbone and the therapeutic agent, the distribution and overall concentration of the therapeutic agent, and the D:L ratio also affect hydrolysis. The D:L ratio can be altered by manipulating the bacterial growth media.

SYNTHESIS

The conjugates of the invention are made by linking a therapeutic agent to a polyamino acid backbone.

Polyamino acids are obtained from fermentation. To produce poly-γ-glutamic acid by fermentation, *B. licheniformis* is grown in a medium containing glycerol and citric acid as carbon sources, ammonium chloride as a nitrogen source, and glutamic acid, magnesium sulfate, ferric chloride, manganese sulfate, and potassium phosphate. See, e.g., Thorne, C. B., et al. *J. Bacteriol.* 68:307 (1954), and Borbely, et al., *Polymer Bulletin* 32:127–132 (1994). *B. licheniformis* can be grown to produce varying amounts of D— and L-poly-γ-glutamic acid, e.g., by using varying amounts of Mn(II) in the growth medium. *B. Anthracis* produces large proportions of D-poly-γ-glutamic acid. See, e.g., Shah, D. et al., *Polymer Preprints*, Washington D.C. Meeting, Vol. 33, No. 2, pp. 488–489 (1992) and Kubota et al., U.S. Pat. No. 5,118,784.

The single free carboxylic acid moiety on each amino acid of a polyamino acid can be reacted directly with a therapeutic agent having an amino, hydroxyl, or thiol group. For example, deoxyspergualin has a reactive amino group, and piroxicam has a free hydroxyl group. Piroxicam can thus be condensed with the carboxylic acid of poly-γ-glutamic acid to form an ester. Alternatively, a free carboxylic acid moiety on the polyamino acid can be first converted to an active ester via 2-ethyl-5-phenylisoxazolium-3'-sulfonate (Woodward's Reagent K), and then reacted with a nucleophile such as a primary amine. Both carbodiimide and chloroformate chemistry can be used to couple a therapeutic agent to a polyamino acid backbone. Additional coupling reagents and reaction conditions are be found in M. Bodanzky, PRINCIPLES OF PEPTIDE SYNTHESIS, (1984) Springer-Verlag, and Bodanzky and Bodanzky, PRACTICE OF PEPTIDE SYNTHESIS (1984) Springer-Verlag.

The following specific examples are offered by way of illustration, and not by way of limitation.

EXAMPLE 1

Formation of a Neutral Red-PGA Derivative

Neutral Red (Sigma Chemical Co., St. Louis, Mo.) was purified by dissolution in water, followed by centrifugation and filtration. Poly-γ-glutamic acid (PGA) (98.7 mg) was stirred in 10.0 mL water, then filtered. The average molecular weight of this batch of PGA was measured twice, resulting the values of 261 kD and 253 kD. Two milliliters of the filtrate was diluted with 8.0 mL water to give a solution with a pH of 5.85. Woodward's Reagent K (105.7 mg, Sigma) was added, and the pH adjusted to between 5.5 and 6.5 with addition of concentrated sodium hydroxide. After 30 minutes the pH was 6.2. Three milliliters of the Neutral Red solution was added. The mixture was stirred for 30 minutes, then placed in a dialysis membrane with a 10–12 kD molecular weight cut-off (MWCO), and dialyzed for 24 hours against water which had been adjusted to pH 4 with HCl.

Following extensive dialysis (72 hours), a gummy brown solid was obtained. A small amount of this solid, dissolved in water, exhibited a UV-VIS spectrum similar to that of the underivatized dye. However, a slight difference in spectrum was noted. At low pH, absorbance at 520 nm dominates, while at high pH, absorbance at 460 nm dominates. Compared with the underivatized dye, the conjugate showed a greater susceptibility to deprotonation. The spectral shift indicated that the dye had been chemically altered, i.e, had been conjugated.

EXAMPLE 2

Formation of a Piroxicam-PGA Derivative in Aqueous Solution

PGA (196 mg) was dissolved in 20 mL water, centrifuged, and the supernatant filtered with 25 mL additional water through a 0.2 μm filter. 2-[N-morpholineo] ethanesulfonic acid (MES) buffer (495 mg) (Sigma Chemicals, St. Louis, Mo.) was added. The pH was adjusted to 6.1 with concentrated sodium hydroxide. Piroxicam (0.50 g) (Sigma) and 0.51 g 1-ethyl-3-(3-dimethyl aminopropyl)-carbodiimide (Sigma) were added. After stirring 1.5 h, the temperature was gradually raised to 70° C. The suspension was transferred into a dialysis tube (10–12 kD MWCO) with 25 mL water. Dialysis against 3 L 0.1% acetic acid for 2 hours was followed by dialysis 3 times against 3 L water for 4 hours. Following lyophilization, the UV spectrum of the product in dimethylsulfoxide was examined. The spectral shift indicated that piroxicam had been chemically altered, i.e, had been conjugated to the backbone.

EXAMPLE 3

Formation of a Piroxicam-PGA Derivative in Organic Solution

PGA (109 mg), 265 mg piroxicam, and 259 mg 1-ethyl-3-(3-dimethyl aminopropyl)carbodiimide were dissolved in 20 mL tetrahydrofuran and stirred under nitrogen at room temperature for 1 hour. The tetrahydrofuran was evaporated, and the solid material transferred into dialysis tubing (10–12 kD MWCO) with 25 mL water. The suspension was dialyzed against 2 L water for one overnight period, and two subsequent four-hour periods.

EXAMPLE 4

Mouse Model of Systemic Lupus Erythematosus (SLE)

MRL/lpr mice are an accepted animal model for systemic lupus erythematosus. Thirteen-week old MRL/lpr mice are subcutaneously implanted with a 50% loaded conjugate in formulations that last approximately 4 weeks. Dosages range between subtherapeutic and therapeutic amounts, e.g., 0, 0.25, 0.5, 1, 2, and 5 mg/kg-day. The animals are sacrificed at 17 weeks. Analysis includes measurements of anti-DNA antibodies, circulating immune complexes, IgG-producing cells in the spleen, presence of IgG in the kidney, macrophage superoxide function, and FACCS (measurement of macrophage activation via ED1, ED2, and ED3 expression). The results of the above analysis indicate that the therapeutic agent is targeted to circulating antigen-processing cells, and effectively treats SLE in mice. See, also, Ito, S., et al., *Clin, Exp. Immunol.* (1990) 81:446.

Use

Conjugates of the invention can be used to deliver one or more therapeutic agents to antigen-processing cells. Thus, diseases mediated by antigen-processing cells can be treated with conjugates of the invention, where the conjugate includes an appropriate therapeutic agent. The invention therefore encompasses methods of treating autoimmune diseases, diseases which activate the immune system, and chronic inflammatory diseases.

For example, macrophages are implicated in degenerative and inflammatory conditions, e.g., autoimmune encephalitis, H. Lassmann, et al., *Glia* 7:19 (1993), C. F. Brosnan, et al., *J. Immunol.* 126:614 (1981); rheumatoid arthritis, L. S. Wilkinson, et al., *Ann. Rheum. Dis.* 52:182 (1993); emphysema, H. A. Chapman, *Ann. N.Y. Acad. Sci.* 624:87 (1991); streptozocin-induced diabetes, M. E. Oschilewski, et al., *Immunol. Lett.* 12:289 (1986); and uveitis, S. M. Whitcup, et al., *Ann. of N.Y. Acad. Sci.*, 696:307 (1993), S. Lightman, et al., IMMUNOLOGY OF EYE DISEASES (Kluwer Academic, Lancaster, Pa.), pp. 87–99. Further examples are psoriasis, silicosis, diabetes type I, polymyositis, coronary heart disease, pernicious anemia, pemphigus vulgaris, encephalitis, ulcerative colitis, Sjögren's syndrome, scleroderma, and mixed connective tissue disease.

In one aspect, the invention features methods for treating an inflammatory disease in a mammal such as a human. According to this aspect, an effective amount of an antigen-processing cell-targeted conjugate is administered to the mammal. For example, the invention features a method of treating an inflammatory disease in a mammal by administering to the mammal an effective amount of a conjugate having the formula: H—{—NH—C*H (—X$^m$M$^{m'}$Y$^{m''}$)—(CH$_2$)$_n$—(C=O)—}$_p$—OH, as defined above. In one embodiment, the disease is an autoimmune disease; in another embodiment, the disease is systemic lupus erythematosus. In a third embodiment, the disease is selected from the group consisting of rheumatoid arthritis, uveitis, psoriasis, type I diabetes, silicosis, polymyositis, coronary heart disease, pernicious anemia, pemphigus vulgaris, encephalitis, ulcerative colitis, Sjögren's syndrome, scleroderma, mixed connective tissue disease, and emphysema.

The form of administration is by methods known to those in the art, including oral administration, topical administration, intranasal administration, parenteral injection, subcutaneous implantation, and aerosol administration (e.g., intrapulmonary). The effective amount of the conjugate varies depending upon the manner of administration, the age and the body weight of the subject, and the condition of the subject to be treated. The effective amount will ultimately be decided by the attending physician or veterinarian. Such amount of the conjugate as determined by the attending physician or veterinarian is referred to herein as "effective amount." Typical dosage ranges are from about 0.1 to about 50 mg/kg of body weight per day, given in 1–4 divided doses. Each divided dose may contain the same or different conjugates of the invention. The dosage will depend on several factors including the overall health of a patient, and the formulation and route of administration of the selected compound(s). The invention also encompasses a packaged drug, containing a pharmaceutical composition formulated into individual dosages and printed instructions, e.g., for self-administration.

Conjugates of the invention are stored or administered in the form of pharmaceutically acceptable salts, such as sodium salts of carboxylic acids, or anionammonium salts of amines. Pharmaceutically acceptable salts can be formed with one or more equivalents of hydrogen chloride, hydrogen bromide, trifluoroacetic acid, and other reagents known to those in the art of drug formulation. Compounds of the invention can be formulated into pharmaceutical compositions by admixture with pharmaceutically acceptable non-toxic excipients and carriers. A pharmaceutical composition of the invention might also contain other therapeutic moieties not encompassed by the invention, such as analgesic, steroidal anti-inflammatory, or anti-cancer agents.

A conjugate of the invention can be administered in unit dosage form, and can be prepared by any of the methods well known in the pharmaceutical art, for example, as described in *Remingtons' Pharmaceutical Sciences* (Mack Pub. Co., Easton, Pa., 1980). Conjugates of this invention may be provided in an aqueous physiological buffer solution containing about 0.1–10% w/v of compound for parenteral administration of a solution or an insoluble suspension. Anti-inflammatory conjugates disclosed herein are prepared for use in parenteral administration, particularly in the form of solutions or liquid suspensions; by subcutaneous implantation; or intranasally, particularly in the form of powders, gels, oily solutions, nasal drops, aerosols, or mists. Subcutaneous implantation is preferred.

Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention can be further obtained, in part, by use of biocompatible biodegradable polymers of lactide, and copolymer of lactide/glycolide or polyoxyethylene/-polyoxypropylene. Additional parenteral delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate.

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. An anti-inflammatory, non-immunogenic conjugate comprising:
   a polyamino acid backbone;
   a multiplicity of molecules of a non-steroidal anti-inflammatory agent; and
   a multiplicity of moieties linking said molecules to said backbone, wherein said polyamino acid backbone has an average molecular weight greater than 250 kD, said polyamino acid backbone comprises greater than 80 percent poly-γ-glutamic acid, said moieties link said molecules of anti-inflammatory agent to said backbone via α-carboxylate groups of the poly-γ-glutamic acid, and said conjugate is preferentially internalized by antigen-processing cells compared to said agent absent the backbone.

2. A conjugate of claim 1, wherein said anti-inflammatory agent is 15-deoxyspergualin, spergualin, piroxicam, or ibuprofen.

3. A conjugate of claim 1, wherein said moiety linking said anti-inflammatory agent to said backbone is an amide bond, an ester bond, or a thioester bond.

4. A conjugate of claim 1, wherein said polyamino acid backbone has a molecular weight between 500 kD and 1500 kD.

5. An anti-inflammatory, non-immunogenic conjugate comprising a derivatized polyamino acid of the formula:

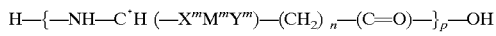

wherein each $X^m$ independently is $C_{1-12}$ alkylene or deleted;

each $M^m$ independently is (C=O)—O, (C=O)—NH, or (C=O)—S, wherein the carbon atom of $M^m$ is bonded either to $X^m$ or, when $X^m$ is deleted, to $C^*$;

each $Y^m$ independently is H, $C_{1-12}$ alkyl, —(CH$_2$)$_a$—O—(CH$_2$)$_b$H, or a nonsteroidal anti-inflammatory agent, wherein at least one $Y^m$ is a nonsteroidal anti-inflammatory agent, and each of a and b independently is an integer between 0 and 12; and p is an integer between 1,900 and 15,000, m is an integer ranging between 1 and p; each n is independently an integer between 1 and 5; said polyamino acid backbone has molecular weight greater than 250 kD; and said conjugate is preferentially internalized by anti-processing cells compared to said agent absent the backbone.

6. A conjugate of claim 5, wherein each $M^m$ independently is (C=O)—O or (C=O)—NH.

7. A conjugate of claim 5, wherein $Y^m$ is 15-deoxyspergualin, spergualin, piroxicam, or ibuprofen.

8. A conjugate of claim 5, wherein n is 2.

9. A conjugate of claim 5, wherein $X^m$ is deleted.

10. A conjugate of claim 5, wherein the stereochemistry of each chiral carbon $C^*$ is L.

11. A conjugate of claim 5, wherein the stereochemistry of each chiral carbon $C^*$ is D.

12. A conjugate of claim 5, wherein p is between 4,000 and 13,000.

13. A conjugate of claim 5, wherein said polyamino acid backbone has a molecular weight between 500 kD and 1500 kD.

14. A method of treating an inflammatory disease in a mammal comprising administering to the mammal an effective amount of a conjugate of claim 1.

15. A method of claim 14, wherein said disease is rheumatoid arthritis, uveitis, psoriasis, type I diabetes, silicosis, polymyositis, coronary heart disease, pernicious anemia, pemphigus vulgaris, encephalitis, ulcerative colitis, Sjögren's syndrome, scleroderma, mixed connective tissue disease, systemic lupus erythematosus, or emphysema.

16. A method of targeting an anti-inflammatory agent to a circulating antigen-processing cell in a mammal, comprising obtaining an anti-inflammatory conjugate comprising a polyamino acid backbone, an anti-inflammatory agent, and a moiety linking said anti-inflammatory agent to said backbone, wherein said polyamino acid backbone has a molecular weight greater than 250 kD; and injecting an amount of said anti-inflammatory conjugate into the mammal, thereby delivering an effective amount of said anti-inflammatory agent to a circulating antigen-processing cell in the mammal.

17. A method of claim 16, wherein said polyamino acid backbone is a poly-γ-glutamic acid backbone.

18. A method of targeting an anti-inflammatory agent to a circulating antigen-processing cell in a mammal, comprising obtaining an anti-inflammatory conjugate of claim 5; and injecting an amount of said anti-inflammatory conjugate into the mammal, thereby delivering an effective amount of said anti-inflammatory agent to a vascularly circulating antigen-processing cell in the mammal.

\* \* \* \* \*